United States Patent
Kamee

(10) Patent No.: US 10,440,295 B2
(45) Date of Patent: Oct. 8, 2019

(54) IMAGE FORMING APPARATUS

(71) Applicant: OLYMPUS CORPORATION, Tokyo (JP)

(72) Inventor: Hiroyuki Kamee, Koganei (JP)

(73) Assignee: OLYMPUS CORPORATION, Tokyo (JP)

(*) Notice: Subject to any disclaimer, the term of this patent is extended or adjusted under 35 U.S.C. 154(b) by 144 days.

(21) Appl. No.: 15/292,260

(22) Filed: Oct. 13, 2016

(65) Prior Publication Data

US 2017/0034457 A1   Feb. 2, 2017

Related U.S. Application Data

(63) Continuation of application No. PCT/JP2015/061140, filed on Apr. 9, 2015.

(30) Foreign Application Priority Data

Apr. 14, 2014   (JP) .................... 2014-083210

(51) Int. Cl.
  *H04N 5/345*  (2011.01)
  *A61B 1/04*  (2006.01)
  (Continued)

(52) U.S. Cl.
  CPC ............ *H04N 5/345* (2013.01); *A61B 1/04* (2013.01); *A61B 1/045* (2013.01); *A61B 1/06* (2013.01);
  (Continued)

(58) Field of Classification Search
  CPC ....... A61B 1/045; A61B 1/043; A61B 1/0638; A61B 1/00009; H04N 5/345
  (Continued)

(56) References Cited

U.S. PATENT DOCUMENTS

2003/0230750 A1* 12/2003 Koyama ........... H01L 29/66757
257/72
2009/0262225 A1 10/2009 Yamaguchi et al.
(Continued)

FOREIGN PATENT DOCUMENTS

JP   2009-297237 A   12/2009
JP   2011-200572 A   10/2011
(Continued)

OTHER PUBLICATIONS

International Search Report dated Jun. 23, 2015 issued in PCT/JP2015/061140.
Neumann, A., "Four-color laser white illuminant demonstrating high color-rendering quality", Optics Express A982 (Jul. 4, 2011), vol. 19, No. S4.
Written Opinion dated Jun. 23, 2015 and International Preliminary Report on Patentability dated Oct. 27, 2016 received in PCT/JP2015/061140.
(Continued)

*Primary Examiner* — Patricia I Young
(74) *Attorney, Agent, or Firm* — Scully, Scott, Murphy & Presser, P.C.

(57) ABSTRACT

An image forming apparatus includes lasers to respectively emit lights having central wavelengths different from each other, an imager to output an image signal upon receiving light from a subject, a laser wavelength-specific image information acquirer to acquire, from the image signal output from the imager, pieces of laser wavelength-specific image information, and an image former to combine the pieces of laser wavelength-specific image information supplied from the laser wavelength-specific image information acquirer, so as to form an observation image in each mode included in the observation modes.

8 Claims, 9 Drawing Sheets

(51) Int. Cl.
*A61B 5/00* (2006.01)
*H04N 9/31* (2006.01)
*A61B 1/00* (2006.01)
*G02B 23/24* (2006.01)
*A61B 1/045* (2006.01)
*A61B 1/06* (2006.01)
*A61B 5/1455* (2006.01)
*H04N 5/225* (2006.01)
*H04N 5/232* (2006.01)
*H04N 5/33* (2006.01)

(52) U.S. Cl.
CPC ........ *A61B 1/0638* (2013.01); *A61B 5/14552* (2013.01); *G02B 23/2469* (2013.01); *H04N 5/2256* (2013.01); *H04N 5/23245* (2013.01); *H04N 5/23293* (2013.01); *H04N 5/332* (2013.01); *H04N 2005/2255* (2013.01)

(58) Field of Classification Search
USPC .......................................... 348/67
See application file for complete search history.

(56) References Cited

U.S. PATENT DOCUMENTS

2012/0157774 A1 6/2012 Kaku
2012/0302847 A1* 11/2012 Ozawa ............... A61B 1/00009
600/339

FOREIGN PATENT DOCUMENTS

JP 2012-125395 A 7/2012
JP 2012-239815 A 12/2012

OTHER PUBLICATIONS

Japanese Office Action dated Apr. 24, 2018 in Japanese Patent Application No. 2014-083210.
Japanese Office Action dated Jan. 8, 2019 in Japanese Patent Application No. 2014-083210.
Japanese Office Action dated Jul. 9, 2019 in Japanese Patent Application No. 2014-083210.

* cited by examiner

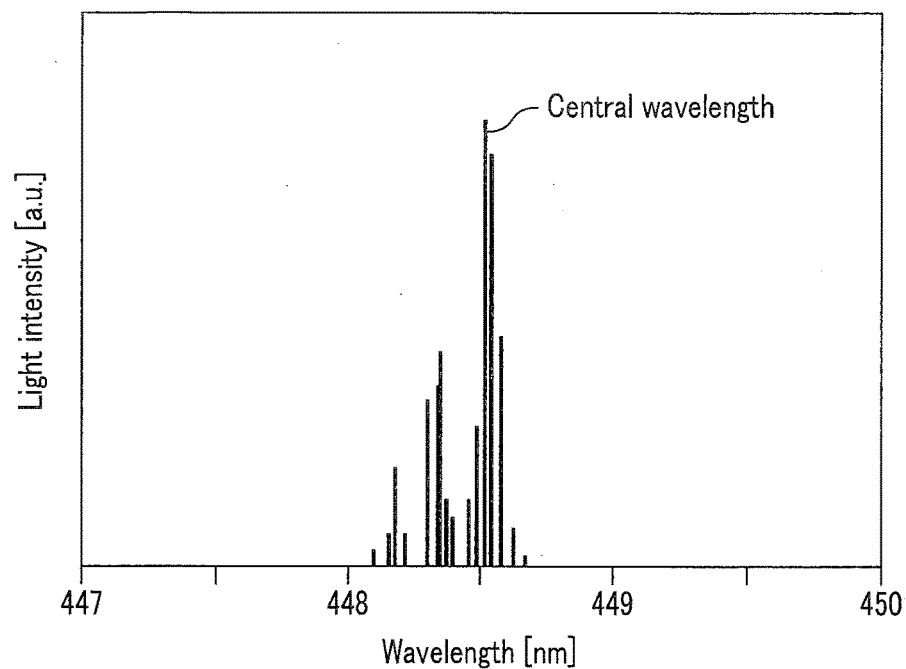
F I G. 2
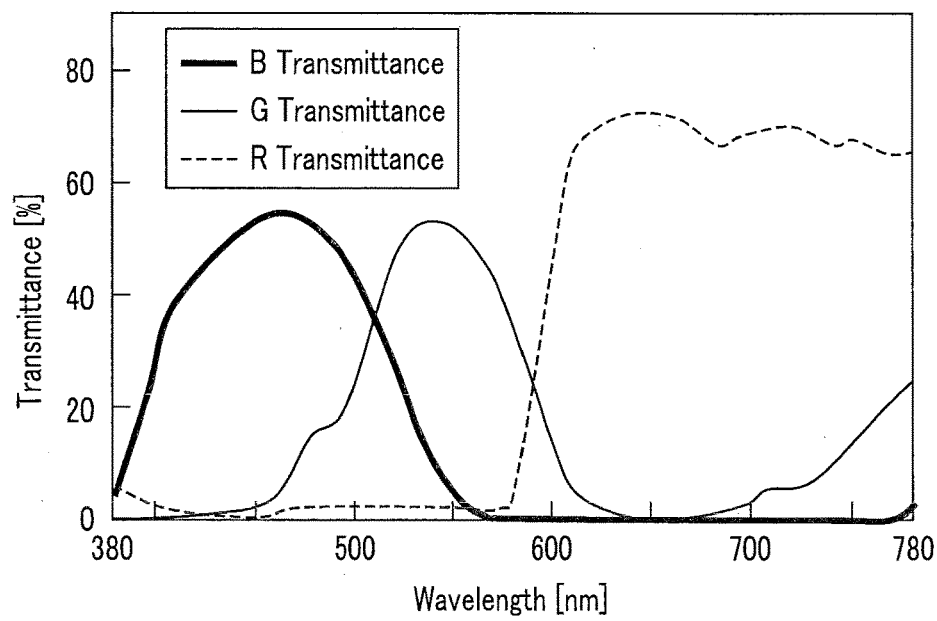
F I G. 3

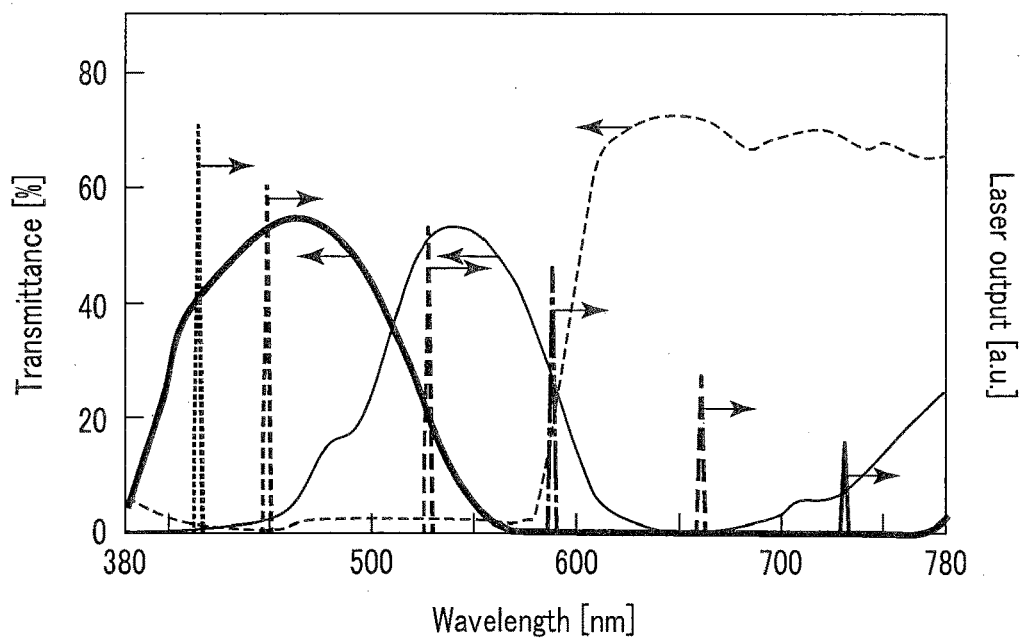
F I G. 10
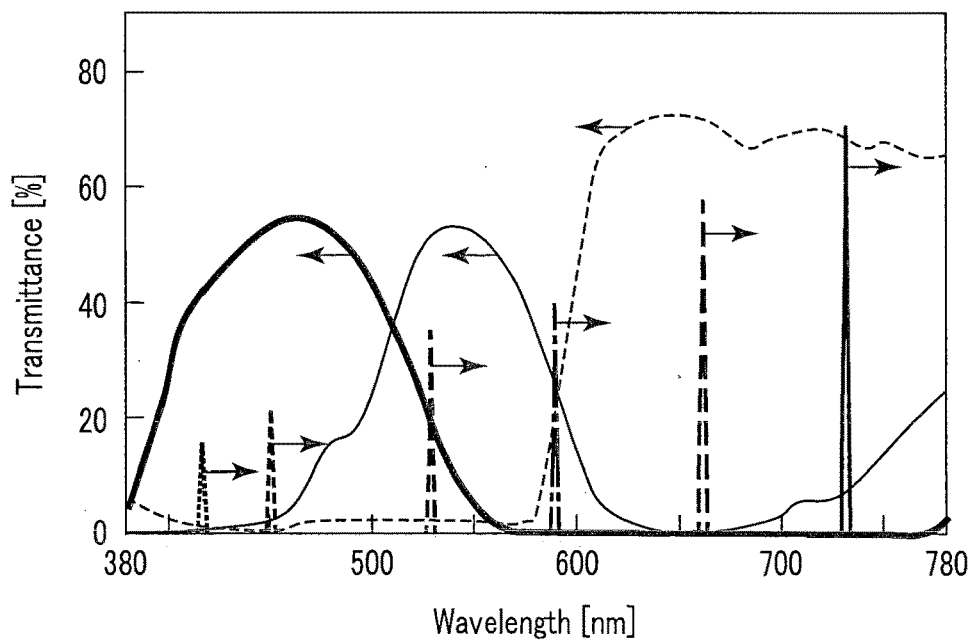
F I G. 11

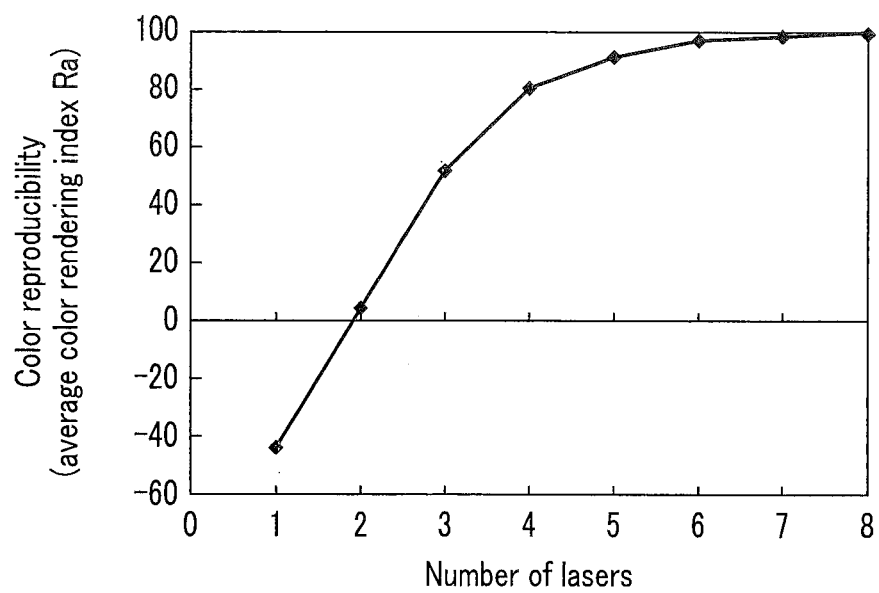
F I G. 13

IMAGE FORMING APPARATUS

CROSS-REFERENCE TO RELATED APPLICATIONS

This application is a Continuation Application of PCT Application No. PCT/JP2015/061140, filed Apr. 9, 2015 and based upon and claiming the benefit of priority from Japanese Patent Application No. 2014-083210, filed Apr. 14, 2014, the entire contents of all of which are incorporated herein by reference.

BACKGROUND OF THE INVENTION

1. Field of the Invention

The present invention relates to an image forming apparatus.

2. Description of the Related Art

In comparison with a gas light source, which has been conventionally used, a solid light source has advantages such as lower power consumption, high connection efficiency, a small size, high-speed switching ability, and others. Technical innovation to such a solid light source is remarkable and, in particular, a solid state laser has very high light density in an emission area and, for example, a so-called fiber light source combined with an optical fiber has been actively developed. The fiber light source is preferable for illuminating the inside of a narrow structure, and its application to an endoscope or the like has been advanced.

For example, Jpn. Pat. Appln. KOKAI Publication No. 2011-200572 provides an electron endoscope system that can simultaneously acquire and simultaneously display two or more types of images by selecting one or two types of images from a microvascular image, an oxygen saturation image, and a vascular image in addition to a white light image by a user or the like.

As a light source configuration, dedicated light sources are arranged for broadband light, a microscopic vascular image, an oxygen saturation image, and a vascular depth image, and the lasers for two types of images among these light sources are caused to emit lights simultaneously or three types of lasers are caused to emit lights sequentially to acquire images.

BRIEF SUMMARY OF THE INVENTION

The present invention is directed to an image forming apparatus to form observation images of a subject in observation modes, the image forming apparatus comprising lasers to respectively emit lights having central wavelengths different from each other that are applied to a subject, an imager to output an image signal upon receiving light from the subject, a wavelength-specific image information acquirer to acquire, from the image signal output from the imager, pieces of wavelength-specific image information with respect to the central wavelengths of the light emitted by the lasers, and an image former to combine the pieces of wavelength-specific image information supplied from the wavelength-specific image information acquirer, so as to form an observation image in each mode included in the observation modes.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 2 shows an example of an emission spectrum of a semiconductor laser;

FIG. 3 shows an example of transmission spectrums of color filters provided on a front surface of a color imager;

FIG. 10 shows a relationship between laser lights emitted during a first sub-frame and color filter spectrums in a second embodiment;

FIG. 11 shows a relationship between laser lights emitted during the second sub-frame and the color filter spectrums in the second embodiment;

FIG. 13 shows a relationship between the number of lasers and color reproducibility.

DETAILED DESCRIPTION OF THE INVENTION

First Embodiment

[Introduction]

It has been conventionally considered that emission of light having no lack of wavelength over entire visible light is required for a white illumination apparatus having high quality and high image reproducibility. However, the development in recent years has revealed that even illumination light that is a combination of single wavelength lights like laser lights can acquire performance (color rendering properties) sufficiently high for the illumination light (A. Neumann et al., Opt. Exp., 19, S4, A982 (Jul. 4, 2011)).

The present inventor has performed a calculation of an average color rending index Ra, which is one of illuminator quality evaluation parameters determined by JIS and the like, to various wavelengths or the number of lasers. Consequently, as shown in FIG. 13, he found out that performance equal to or higher than that of conventionally used general illumination having a broad spectrum can be provided by successfully combining laser lights having different wavelengths.

Consequently, it has been revealed that lasers that can each output light having high light density and parallelism from an emission region far smaller than a conventionally used gas light source or an LED that goes on sale in recent years can be used as a white light observation (normal light observation) light source that requires color rendering properties, and that an advantage of highly efficient introduction into a narrow-diameter light guide member like a fiber can be obtained in an observation apparatus that is assumed to be used for observation in a closed space like an endoscope. Further, when lasers are used for specific light observation that has been actively developed in the field of endoscopes in recent years, it is possible to obtain an advantage that narrow spectral properties of each of the lasers can accurately acquire wavelength characteristics to a specific substance in a target region.

[Configuration]

Figure 1:
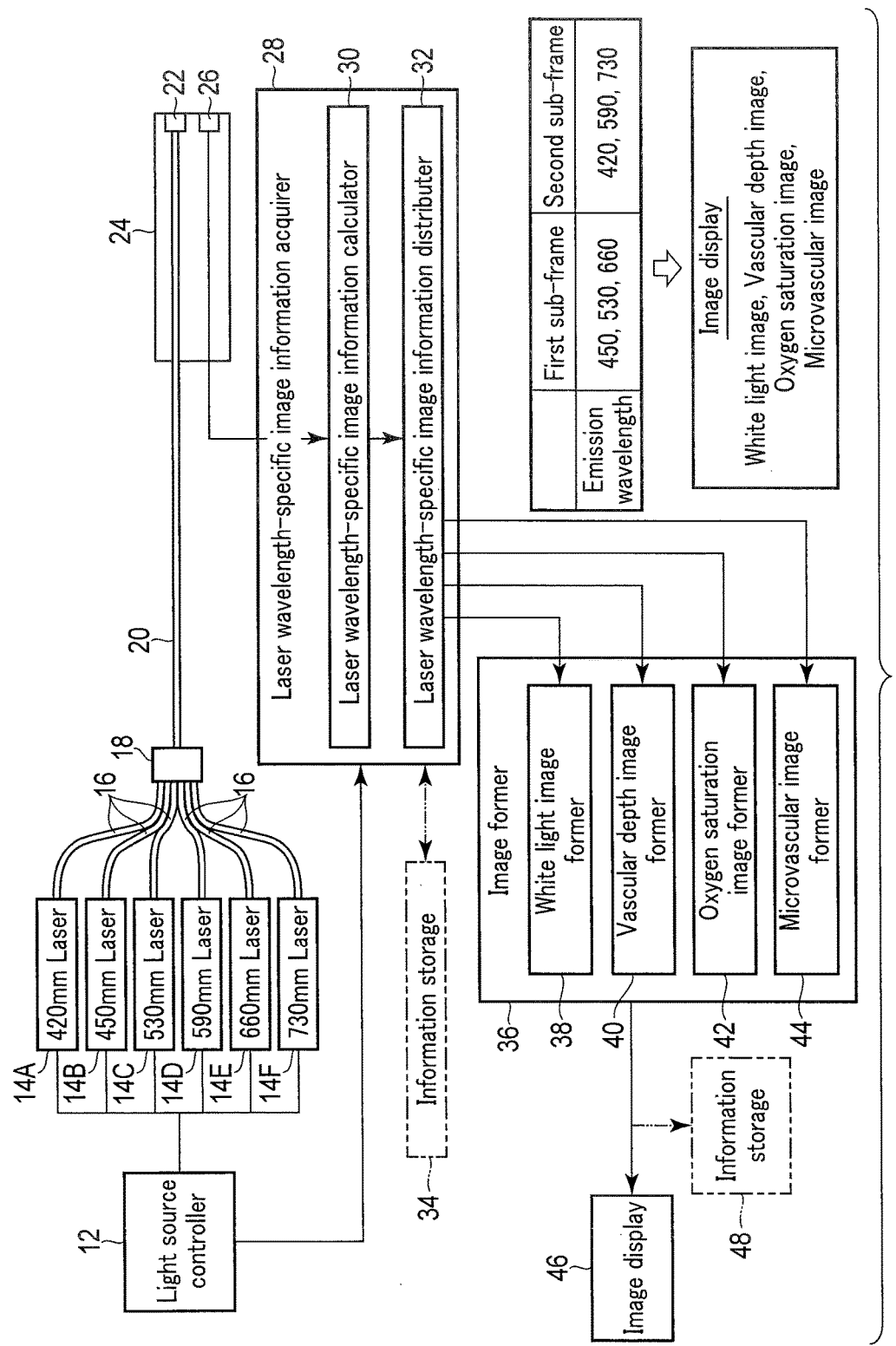
FIG. 1 is an overall schematic view of an image forming apparatus according to a first embodiment.

This image forming apparatus is an image forming apparatus such as an endoscope that is mainly intended to observe "the inside" of a substance into which external light rarely enters. FIG. 1 shows an overall schematic view of the apparatus.

As shown in FIG. 1, the image forming apparatus includes lasers 14A, 14B, 14C, 14D, 14E, and 14F to emit light having central wavelengths difference from each other, a light source controller 12 to control these lasers 14A to 14F, and an irradiator to mix the lights emitted from the lasers 14A to 14F and to apply the mixed light to a subject. It is to be noted that the laser is, e.g., a semiconductor laser, laser oscillation is performed at wavelengths as shown in FIG. 2, and oscillation wavelengths including the shortest one to the longest one are included in a wavelength region of approximately several nm. FIG. 2 is an example of an emission spectrum of a semiconductor laser to emit light at a wavelength of approximately 448.5 nm. The emission spectrum has tens of line spectrum components, and a ratio and/or the number of line spectrums vary with time. A width of the wavelength region of the emission spectrum has an expanse of approximately 1 nm as a whole. A central wavelength of narrow band light when multimode laser light having such a spectrum is used as the narrow band light is defined as a wavelength having a highest light intensity.

The laser 14A can emit light having a wavelength of 420 nm, the laser 14B can emit light having a wavelength of 450 nm, the laser 14C can emit light having a wavelength of 530 nm, the laser 14D can emit light having a wavelength of 590 nm, the laser 14E can emit light having a wavelength of 660 nm, and the laser 14E can emit light having a wavelength of 730 nm, respectively.

The light source controller 12 can control outputs, output timings, and output periods of the laser 14A to 14F.

The irradiator is constituted from optical fibers 16 optically coupled with the lasers 14A to 14F, respectively, a combiner 18 to combine lights guided through the optical fibers 16, an optical fiber 20 to guide the light combined by the combiner 18, and an illumination light distribution converting member 22 optically coupled with the optical fiber 20.

The illumination light distribution converting member 22 is arranged at a distal end portion of a scope insertion section 24, the optical fiber 20 enters the inside of the scope insertion section 24 from the outside and extends to the illumination light distribution converting member 22.

The illumination light distribution converting member 22 may be constituted of, e.g., a lens, a surface diffusion member having a light diffusing function provided on a member surface, an inner diffusion member containing micro members with different refractive indexes and/or reflectances, and a composite optical member having a combination of these functions.

The image forming apparatus comprises a color imager 26 to receive light from a subject and to output an image signal, a laser wavelength-specific image information acquirer 28 to acquire, from the image signal output from the color imager 26, pieces of laser wavelength-specific image information corresponding to central wavelengths of lights emitted from the lasers 14A to 14F, an image former 36 to combine the pieces of laser wavelength-specific image information supplied from the laser wavelength-specific image information acquirer 28, so as to form an observation image in each observation mode, and an image display 46 to display an image formed by the image former 36.

The image former 36 has image formers corresponding to observation modes, respectively. Here, the observation mode means a type of an observation technique to obtain specific information in optical information of the subject. In this embodiment, the observation modes includes a normal observation mode, a vascular depth observation mode, an oxygen saturation observation mode, and a microvascular observation mode, and the image former 36 has a white light image former 38, a vascular depth image former 40, an oxygen saturation image former 42, and a microvascular image former 44 in correspondence with these observation modes.

The laser wavelength-specific information acquirer 28, which can acquire information concerning the lasers 14A to 14F from the light source controller 12, includes a laser wavelength-specific image information calculator 30 to calculate pieces of laser wavelength-specific image information from the image signal output from the color imager 26, and a laser wavelength-specific image information distributer 32 to select laser wavelength-specific image information required for each observation mode from the pieces of laser wavelength-specific image information calculated by the laser wavelength-specific image information calculator 30 and to distribute and transmit it to the image former 38, 40, 42, or 44 corresponding to each observation mode.

The laser wavelength-specific image information distributer 32 has a function of storing a combination of the lasers suitable for each observation mode, and distributes and transmits the laser wavelength-specific image information required for each observation mode to the image former 38, 40, 42, or 44 in the image former 36 in accordance with information of the combination of the lasers.

The image forming apparatus may also include an information storage 34 to store the pieces of laser wavelength-specific image information acquired by the laser wavelength-specific image information acquirer 28, and an information storage 48 to store an observation image formed by the image former 36, as needed.

Since functions implemented by the laser wavelength-specific information acquirer 28 and the image former 36 are arithmetic processing of the acquired image signal, such functions can be implemented by circuits and/or processors including hardware.

[Operation]

Lights emitted from the lasers 14A to 14F are guided through the optical fiber 16 connected to the lasers 14A to 14F, enter the combiner 18, and are combined. The combined light is guided through an optical fiber 20, and enters the illumination light distribution conversion member 22 installed at a distal end of the scope insertion section 24. Light distribution of the combined light that has entered the illumination light distribution conversion member 22 is adjusted to be suitable for subject observation, and the combined light is applied to the subject that is present ahead.

The exiting combined light turns to returning light containing reflection spectrum characteristics peculiar to the subject that is present ahead, and a part of the light enters the color imager 26 that is an imager.

In the color imager 26, color-specific imaging elements having different wavelength sensitivities of R (red), G (green), and B (blue) are arranged on the same plane in a regular manner, and receive pieces of color-specific intensity information to the returning light in accordance with each pixel.

Here, FIG. 3 shows an example of transmission spectrums of color filters provided on a front surface of the color imager 26.

<Drive Method>

In this embodiment, one frame is constituted of sub-frames of two periods, i.e., a first sub-frame and a second sub-frame. Here, one frame means one period during which all of still picture (frame) information constituting a unit to a selected observation mode (a moving image) is acquired.

During the first sub-frame, the laser 14B to emit light having a wavelength of 450 nm, the laser 14C to emit light having a wavelength of 530 nm, and the laser 14E to emit light having a wavelength of 660 nm are turned on.

During the second sub-frame, the laser 14A to emit light having a wavelength of 420 nm, the laser 14D to emit light having a wavelength of 590 nm, and the laser F to emit light having a wavelength of 730 nm are turned on.

Figure 4:
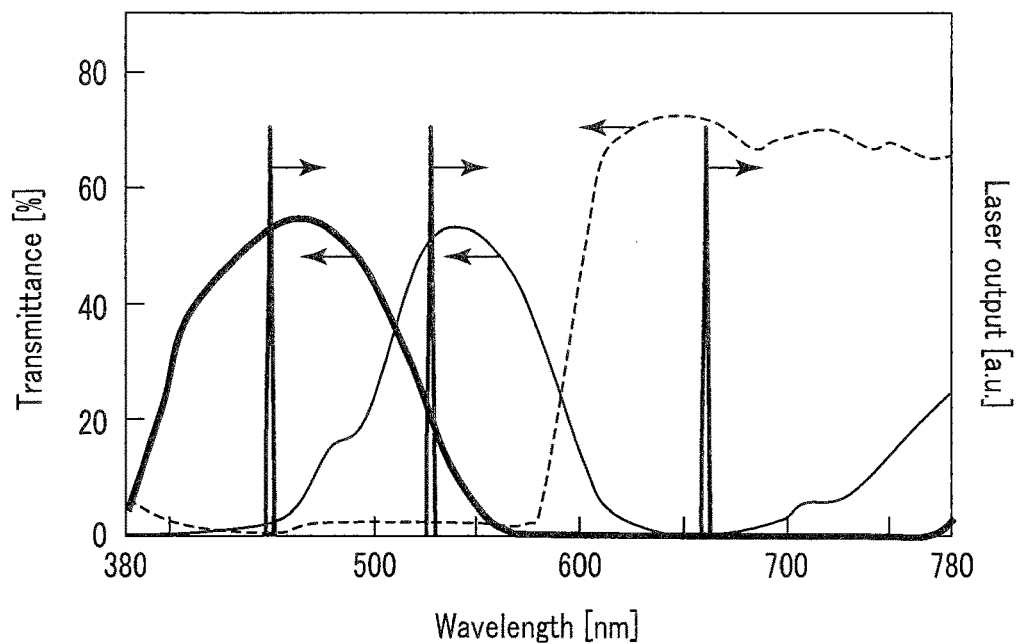
FIG. 4 shows a relationship between laser lights emitted during a first sub-frame and color filter spectrums.
Figure 5:
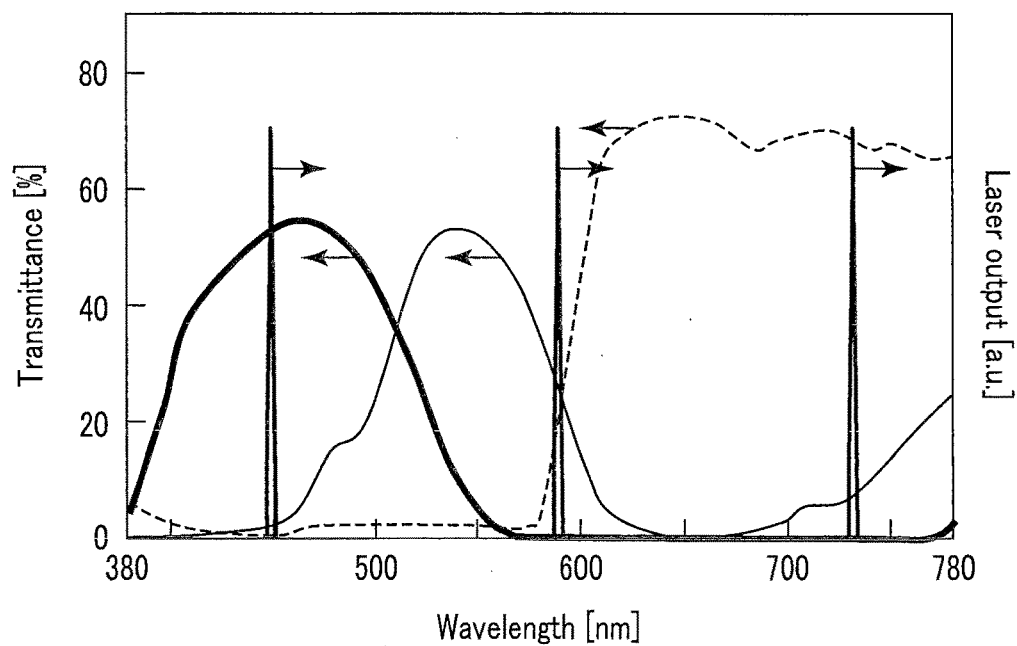
FIG. 5 shows a relationship between laser lights emitted during a second sub-frame and color filter spectrums.

FIG. 4 shows a relationship between laser lights emitted during the first sub-frame and color filter spectrums, and FIG. 5 shows a relationship between laser lights emitted during the second sub-frame and the color filter spectrums.

<Observation Modes>

In this embodiment, it is possible to select a total of four types, i.e., the normal observation mode, the vascular depth observation mode, the oxygen saturation observation mode, and the microvascular observation mode.

In the normal observation mode, a white light image (a normal light image) is constructed from three pieces of laser wavelength-specific image information of 450 nm, 530 nm, and 660 nm.

In the vascular depth observation mode, a vascular depth image is constructed from two pieces of laser wavelength-specific image information of 450 nm and 730 nm.

In the oxygen saturation observation mode, an oxygen saturation image is constructed from two pieces of laser wavelength-specific image information of 590 nm and 660 nm.

In the microvascular observation mode, a microvascular image is constructed from one piece of the laser wavelength-specific image information of 420 nm.

The observation modes mean types of observation techniques to provide specific information in optical information of a subject, e.g., a normal observation image or a specific light observation image by applying one or more lights in different wavelength bands as described above.

The white light image is constructed from the laser wavelength-specific information (an image) of 450 nm, the laser wavelength-specific image information (an image) of 530 nm, and the laser wavelength-specific image information (an image) of 660 nm, which are calculated from the first sub-frame.

The vascular depth image is constructed from the laser wavelength-specific image information (an image) of 450 nm, which is calculated from the first sub-frame, and the laser wavelength-specific image information (an image) of 730 nm, which is calculated from the second sub-frame.

The oxygen saturation image is constructed from the laser wavelength-specific image information (an image) of 590 nm, which is calculated from the second sub-frame, and the laser wavelength-specific image information (an image) of 660 nm, which is calculated from the first sub-frame.

The microvascular image is constructed from the laser wavelength-specific image information (an image) of 420 nm, which is calculated from the second sub-frame.

As described above, a part of the wavelength-specific image information used for formation of an observation image in a given observation mode is used for formation of an observation image in another observation mode. Specifically, the wavelength-specific image information of 450 nm used for formation of a white light observation image in the normal observation mode is also used for formation of a vascular depth image in the vascular depth observation mode.

The observation modes are not restricted to the four types. Other observation modes may be further selectable. It is satisfactory if at least two types of observation modes are selectable.

The wavelengths in the respective observation modes are not restricted to the above example either. Combinations of the wavelengths assigned to the respective sub-frames are not restricted to the above example either. It is desirable to appropriately select combinations that can be detected by wavelength separation using color filters and the like.

To achieve this, it is important to set the number of wavelengths to be equal to or less than at least the number of types of color filters. For example, when the color imager 26 can separate and detect mainly three colors like RGB or CMY, lights applied during one sub-frame should be lights of three wavelengths or less. Such a setting enables creating three simultaneous linear equations from output data of one pixel with three colors, thus providing each laser wavelength-specific image information.

Then, wavelengths dispersed in a visible light region should be selected. When lasers whose wavelengths are extremely close to each other are simultaneously turned on, wavelength sensitivity characteristics of the imager hardly vary during the period, and hence finding an independent solution with less errors is difficult. It is desirable for the wavelengths of the lights emitted from the lasers that are simultaneously turned on to be apart from each other by at least 10 nm or more, or more desirably 20 nm or more.

For example, in a case where two lasers emit lights having wavelengths in the range of 450 nm, lighting periods of these lasers should be assigned to different sub-frames, and they should be turned on with lasers to emit lights having other wavelengths.

As characteristics of the lasers, emission wavelength widths are very narrow, and the wavelengths are stable. On the basis of these characteristics, since a transmittance of the color filter for a corresponding wavelength and light receiving sensitivity of the imager are relatively easily grasped, if the number of the lasers that are simultaneously turned on is equal to or less than the number of color separations included in the imager, the number of pieces of data provided by the imager in accordance with each pixel is also "3", and hence one type of solution is found for the reflectance of the light having each laser wavelength in each picture element, (which means one pixel in one set of RGB color pixels).

<Calculation Method 1>

An example of a calculation method of the laser wavelength-specific image information performed by the laser wavelength-specific image information calculator 30 will now be described. This calculation method is a simple calculation method.

In an image signal acquired during each sub-frame, RGB color pixel image information or a result of constant multiplication of the information is determined as laser wavelength-specific image information.

That is, since wavelengths of lights emitted by three lasers that are turned on during the first sub-frame are in a band where sensitivities of corresponding color pixels are maximum and sensitivities to non-corresponding pixels are very low, the RGB color pixel image information can be determined as 450-nm image information, 530-nm image information, and 660-nm image information with no change.

On the other hand, 420 nm and 590 nm in wavelengths of lights emitted by three lasers that are turned on during the second sub-frame are not lights in a band where sensitivities of the B color pixel and the G color pixel are maximum. However, since all of the three lasers have low sensitivities to non-corresponding pixels, results of multiplying the B color image information and the G color image information acquired during the second sub-frame by constants corresponding to wavelength-specific sensitivities can be determined as a 420-nm image, a 590-nm image, and a 730-nm image, respectively.

In a narrow sense, since the R color image information has sensitivity in a wavelength band of 590 nm, when the R color image in the second sub-frame is used as it is, the image is affected by data of the lights of not only 730 nm but also 590 nm, and hence it is not accurate. In such a case, the image is allowed to be close to a more accurate value by subtracting a constant multiple of the G color image information including the 590-nm color image information from the R color image including the wavelength image information of both 590 nm and 730 nm.

<Calculation Method 2>

Another example of the calculation method of the laser wavelength-specific image information performed by the laser wavelength-specific image information calculator 30 will now be described.

Wavelengths of lights emitted by three lasers that are turned on during one sub-frame are assumed to be L (nm), M (nm), and N (nm), respectively.

Light quantities of the lights emitted by the three lasers that are turned on during one sub-frame are assumed to be $I_L$ (W), $I_M$ (W), and $I_N$ (W), respectively.

Light receiving sensitivity characteristics of respective three types of color pixels RGB including color filter transmittances or light receiving sensitivity characteristics of the imager are assumed to be R (A/W), G (A/W), and B (A/W), respectively.

Light receiving sensitivity characteristics with respect to the applied lights having the three laser wavelengths in the light receiving sensitivity characteristics of the respective color pixels are assumed to be $R_L$ (A/W), $R_M$ (A/W), $R_N$ (A/W), $G_L$ (A/W), $G_M$ (A/W), $G_N$ (A/W), $B_L$ (A/W), $B_M$ (A/W), and $B_N$ (A/W), respectively.

Reflection characteristics of a subject as a target with respect to the lights having three laser wavelengths are assumed to be $S_L$ (%), $S_M$ (%), and $S_N$ (%), respectively.

Ratios of lights that effectively enter the imager in light reflected from the subject as the target are assumed to be $V_L$ (%), $V_M$ (%), and $V_N$ (%), respectively.

As a result of imaging, signal values acquired in accordance with each of three types of color pixels RGB are assumed to be $D_R$ (A), $D_G$ (A), and $D_B$ (A), respectively.

These parameters meet the following relationships.

$$D_R = I_L \times S_L \times V_L \times R_L + I_M \times S_M \times V_M \times R_M + I_N \times S_N \times V_N \times R_N$$

$$D_G = I_L \times S_L \times V_L \times G_L + I_M \times S_M \times V_M \times G_M + I_N \times S_N \times V_N \times G_N$$

$$D_B = I_L \times S_L \times V_L \times B_L + I_M \times S_M \times V_M \times B_M + I_N \times S_N \times V_N \times B_N$$

In these expressions, $I_L$, $V_L$, $R_L$, $I_M$, $V_M$, $R_M$, $I_N$, $V_N$, $R_N$, $I_L$, $V_L$, $G_L$, $I_M$, $V_M$, $G_M$, $I_N$, $V_N$, $G_N$, $I_L$, $V_L$, $B_L$, $I_M$, $V_M$, $B_M$, $I_N$, $V_N$, and $B_N$ can be grasped in advance, and $D_R$, $D_G$, and $D_B$ can be acquired in connection with the respective pixels by imaging. Thus, the above relational expressions are three simultaneous linear expressions in which only three types of unknowns, i.e., $S_L$, $S_M$, and $S_N$ remain, and the laser wavelength-specific reflectance for each pixel can be calculated. When the laser wavelength-specific reflectance is acquired in accordance with each pixel, it can be two-dimensional laser wavelength-specific image information with respect to the subject.

This can be likewise applied to the second sub-frame.

<Imaging>

The color imager 26 performs photoelectric conversion corresponding to a received light quantity, and transmits an electrical signal group to the laser wavelength-specific image information acquirer 28. In the laser wavelength-specific image information acquirer 28, the laser wavelength-specific image information calculator 30 calculates the laser wavelength-specific image information in accordance with the above-described process, and transmits the information to the laser wavelength-specific image information distributer 32.

The laser wavelength-specific image information distributer 32 accumulates the laser wavelength-specific image information transmitted from the laser wavelength-specific image information calculator 30, and appropriately distributes and transmits all pieces of the laser wavelength-specific image information that can be obtained during one frame to the white light image former 38, the vascular depth image former 40, the oxygen saturation image former 42, and the microvascular image former 44 in the image former 36 when all these pieces of the laser wavelength-specific image information are acquired.

The respective image formers 38, 40, 42, and 44 convert the appropriately distributed and received laser wavelength-specific image signals into appropriate pieces of observation image information, and transmit them to the image display 46.

The image display 46 displays all the received four types of image information in a fashion comprehensible a user and others.

Figure 6:
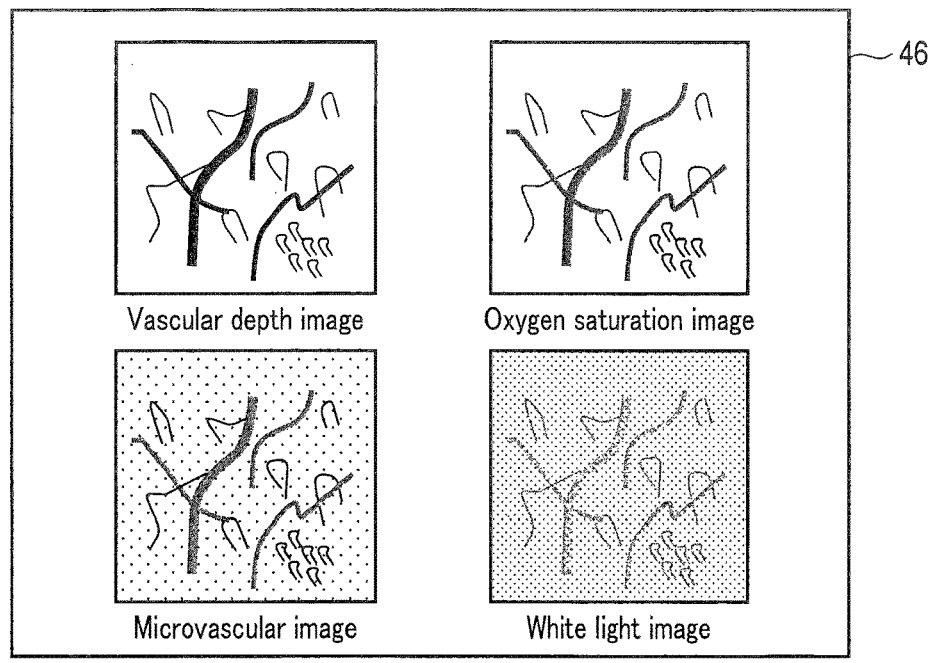
FIG. 6 shows a display example of observation images in an image display.

For example, when all the pieces of image information acquired during one frame are appropriately processed, they are simultaneously displayed. For example, as shown in FIG. 6, one screen in the image display 46 is divided into four, and respective images are arranged in juxtaposition and displayed.

Figure 7:
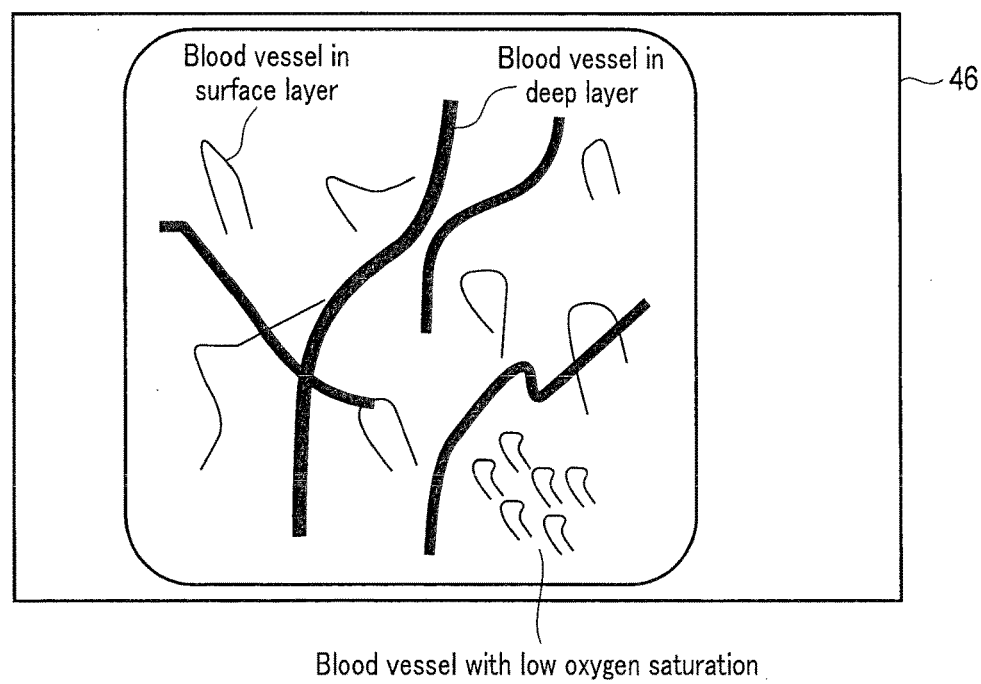
FIG. 7 shows another display example of an observation image in the image display.

As another example, these images are combined and superimposed within one image as shown in FIG. 7, and processing such as color coding, changing in brightness, or blinking is applied and a processed image is displayed so that various kinds of specific information can be provided depending on how to see one screen.

<Image Forming Process 1>

Figure 8:
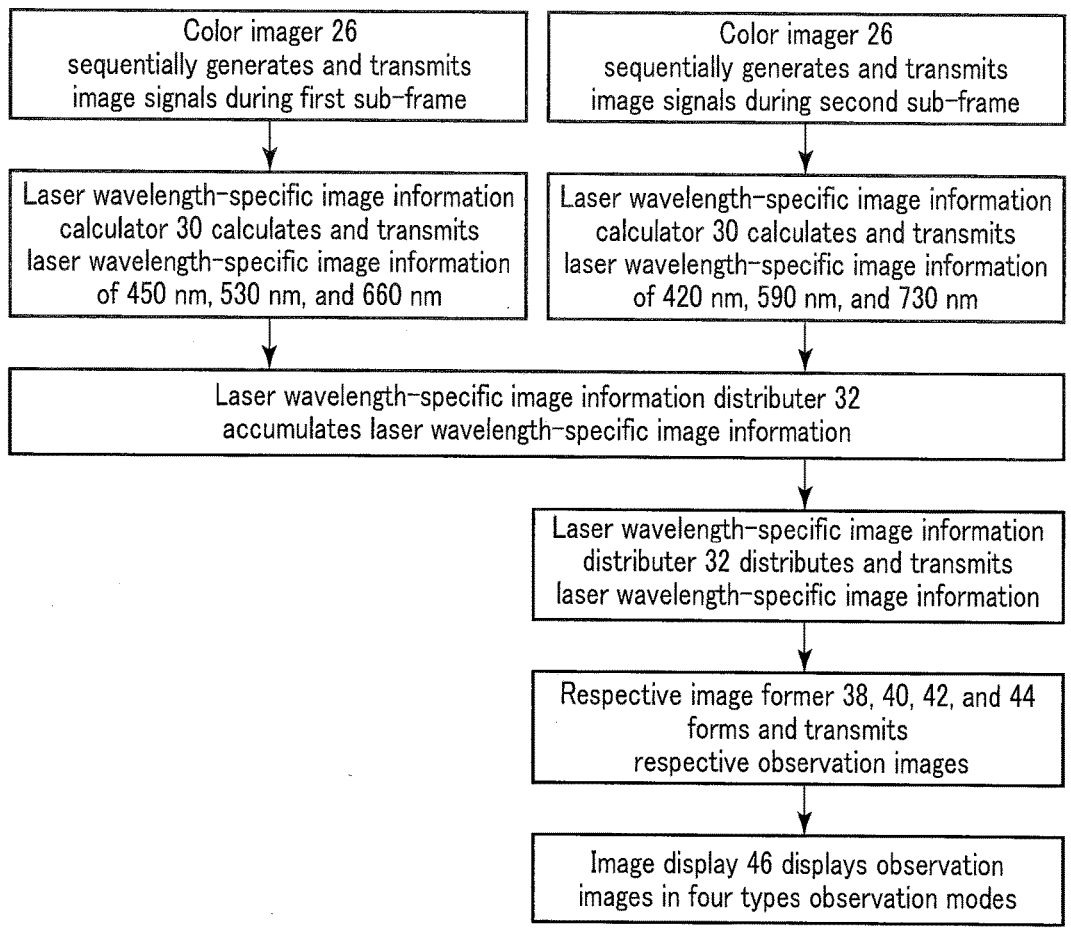
FIG. 8 shows a process flow of image formation according to an example where a laser wavelength-specific image information distributer accumulates laser wavelength-specific image information.

The laser wavelength-specific image information distributer 32, for example, temporarily accumulates the laser wavelength-specific image information, and then distributes and transmits the laser wavelength-specific image information. FIG. 8 shows an example of a process flow of image formation according to the structural example.

During the first sub-frame, the color imager 26 sequentially generates images signals, and transmits them to the laser wavelength-specific image information acquirer 28. The laser wavelength-specific image information calculator 30 in the laser wavelength-specific image information acquirer 28 calculates the laser wavelength-specific image information of 450 nm, 530 nm, and 660 nm, and transmits them to the laser wavelength-specific image information distributer 32. The laser wavelength-specific image information distributer 32 accumulates the received laser wavelength-specific image information in the first sub-frame.

During the second sub-frame, the color imager 26 sequentially generates image signals, and transmits them to the laser wavelength-specific image information acquirer 28. The laser wavelength-specific image information calculator 30 in the laser wavelength-specific image information acquirer 28 calculates the laser wavelength-specific image information of 420 nm, 590 nm, and 730 nm, and transmits them to the laser wavelength-specific image information distributer 32. The laser wavelength-specific image information distributer 32 accumulates the received laser wavelength-specific image information in the second sub-frame.

After receiving the laser wavelength-specific image information in the second sub-frame, the laser wavelength-specific image information distributer 32 distributes and transmits the laser wavelength-specific image information required for the four types of observation modes to the white light image former 38, the vascular depth image former 40, the oxygen saturation image former 42, and the microvascular image former 44 in the image former 36, respectively.

The white light image former 38, the vascular depth image former 40, the oxygen saturation image former 42, and the microvascular image former 44 form observation images in accordance with the received laser wavelength-specific image information and transmits them to the image display 46, respectively.

The image display 46 displays the received observation images in the four types of observation modes.

<Image Forming Process 2>

Figure 9:
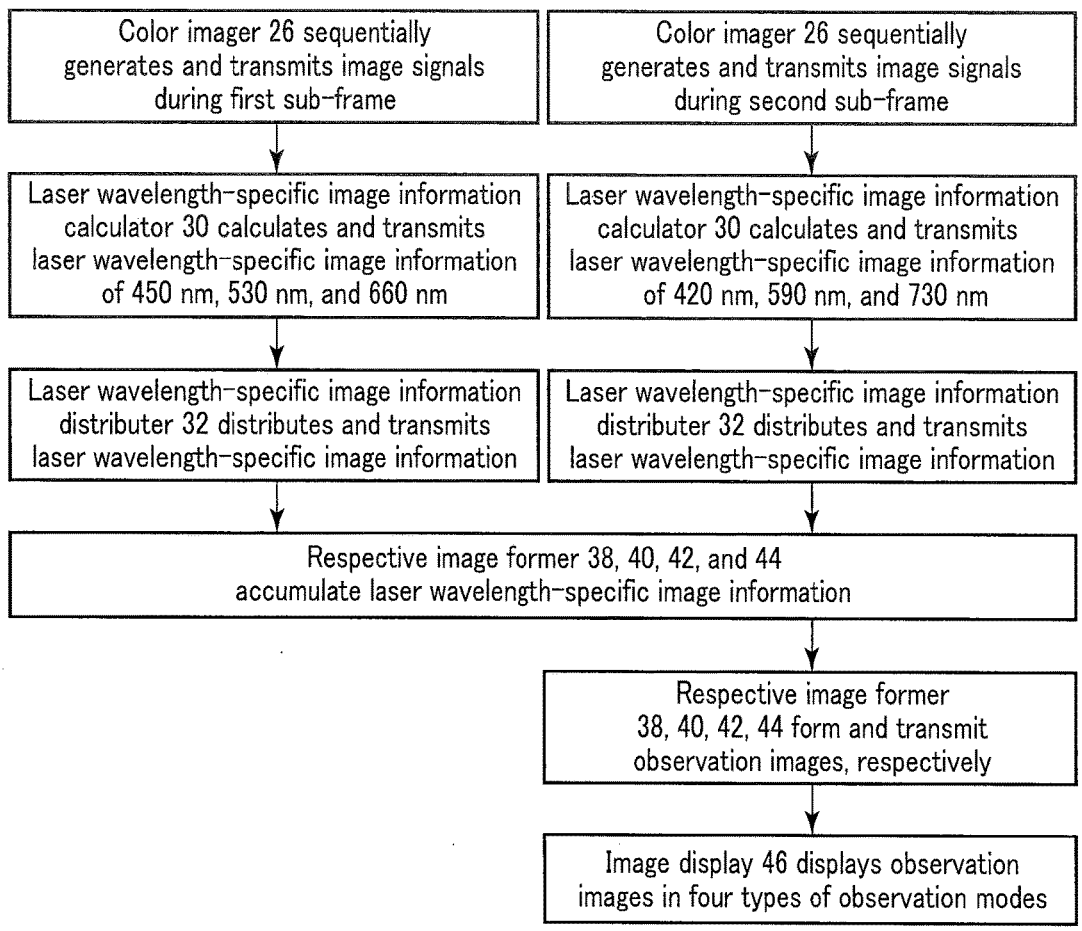
FIG. 9 shows a process flow of image formation according to an example where an image former accumulates laser wavelength-specific image information.

Although the structural example where the laser wavelength-specific image information distributer 32 accumulates the laser wavelength-specific image information has been described above, the image former 36 may accumulate the laser wavelength-specific image information instead of the laser wavelength-specific image information distributer 32 accumulating the laser wavelength-specific image information as another structural example. FIG. 9 shows an example of a process flow of image formation according to the structural example.

During the first sub-frame, the color imager 26 sequentially generates image signals, and transmits them to the laser wavelength-specific image information acquirer 28. The laser wavelength-specific image information calculator 30 in the laser wavelength-specific image information acquirer 28 calculates the laser wavelength-specific image information of 450 nm, 530 nm, and 660 nm, and transmits them to the laser wavelength-specific image information distributer 32. The laser wavelength-specific image information distributer 32 distributes and transmits the laser wavelength-specific image information required by the image formers 38, 40, 42, and 44 in the image former 36 to the image formers 38, 40, 42, and 44, respectively. The respective image formers 38, 40, 42, and 44 accumulate the received laser wavelength-specific image information in the first sub-frame.

During the second sub-frame, the color imager 26 sequentially generates image signals, and transmits them to the laser wavelength-specific image information acquirer 28. The laser wavelength-specific image information calculator 30 in the laser wavelength-specific image information acquirer 28 calculates the laser wavelength-specific image information of 420 nm, 590 nm, and 730 nm, and transmits them to the laser wavelength-specific image information distributer 32. The laser wavelength-specific image information distributer 32 distributes and transmits the laser wavelength-specific image information required by the image formers 38, 40, 42, and 44 in the image former 36 to the image formers 38, 40, 42, and 44, respectively. The respective image formers 38, 40, 42, and 44 accumulate the received laser wavelength-specific image information in the second sub-frame.

After receiving the laser wavelength-specific image information in the second sub-frame, the image formers 38, 40, 42, and 44 form observation images in accordance with the laser wavelength-specific image information in the first sub-frame and the laser wavelength-specific image information in the second sub-frame that have been accumulated, and transmit them to the image display 46, respectively.

The image display 46 displays the received observation images in the four types of observation modes.

[Others]

In order to acquire image information having higher image reproducibility, the same laser may perform irradiation more than once during one frame. More accurate image information can be provided by solving three unknowns with the use of four or more simultaneous linear equations rather than solving the three simultaneous linear equations to the three unknowns as described above.

[Effect]

Since all the observation modes of, e.g., normal light or specific light are constituted by using the lasers, an advantage that light can be highly efficiently introduced into a narrow-diameter light guide member such as a fiber in any mode can be provided, and an improvement in brightness can be greatly improved as compared with an LED or a gas light source.

Since the specific light is formed by using the lasers, as compared with a light source having a broad spectrum such as a gas light source or an LED, image information peculiar to a given wavelength alone can be acquired, and the image reproducibility can be enhanced.

When at least one piece of the laser wavelength-specific image information is used for images, the number of the lasers can be reduced, thereby resulting in a reduction in cost.

Since some of the lasers for specific light are utilized to construct the white light image (the normal light image), the number of the lasers can be decreased, and a reduction in cost and a reduction in volume can be realized.

Since more than one types of the lasers for specific light images are shared, the number of the lasers can be further reduced, and a reduction in cost and a reduction in volume can be realized.

Since at least some of the pieces of the laser wavelength-specific image information used for formation of an observation image in one observation mode are used for formation of an observation image in a different observation mode, a sub-frame for acquisition of the laser-wavelength-specific image information used for formation of the observation image in the different observation mode does not have to be provided, the number of the sub-frames in one frame can be decreased, a frame rate can be increased, and moving image performance can be improved.

Since the number of the sub-frames is smaller than the number of the observation modes, the number of the sub-frames in one frame can be decreased as compared with those in conventional examples. Thus, the frame rate can be increased, and the moving image performance can be improved.

Since the number of the emission light sources is always equal to or less than the number of the color separations in the color imager 26, the laser wavelength-specific image information can be accurately acquired, and the image reproducibility in various observation modes constructed from the information can be improved.

Since the laser wavelength-specific image information calculator 30 is provided, the laser wavelength-specific image information can be accurately acquired, and the image reproducibility in various observation modes constructed from the information can be improved.

Since the laser wavelength-specific image information distributer 32 is provided, the accurate laser wavelength-specific image information can be transmitted to the appropriate image former 36 at appropriate timing, so that the observation mode image reproducibility is improved.

Since the number of the lasers that are simultaneously turned on is always equal to or less than the number of color separations, conversion into the laser wavelength image information that is more accurate than the known color filter/imager characteristics is enabled, and an observation mode image with the high image reproducibility can be constructed.

Second Embodiment

In this embodiment, more lasers than the number of types of color filters are turned on at a time.

The configuration of an image forming apparatus and observation modes are the same as those in the first embodiment. In particular, the color imager 26 is a color imager having color pixels of RGB.

[Operation]
<Drive Method>

In this embodiment, one frame is constituted of sub-frames of two periods, i.e., a first sub-frame and a second sub-frame.

During the first sub-frame, a laser 14A to emit light having a wavelength of 420 nm, a laser 14B to emit light having a wavelength of 450 nm, a laser 14C to emit light having a wavelength of 530 nm, a laser 14D to emit light having a wavelength of 590 nm, a laser 14E to emit light having a wavelength of 660 mm, and a laser 14F to emit light having a wavelength of 730 nm are turned on. FIG. 10 shows a relationship between laser lights applied during the first sub-frame and color filter spectrums.

During the second sub-frame, the laser 14A to emit light having the wavelength of 420 nm, the laser 14B to emit light having the wavelength of 450 nm, the laser 14C to emit light having the wavelength of 530 nm, the laser 14D to emit light having the wavelength of 590 nm, the laser 14E to emit light having the wavelength of 660 mm, and the laser 14F to emit light having the wavelength of 730 nm are turned on with laser outputs different from those in the first sub-frame. FIG. 11 shows a relationship between laser lights applied during the second-sub frame and color filter spectrums.

As can be understood from FIG. 10 and FIG. 11, during both the first sub-frame and the second sub-frame in one frame, all the lasers 14A to 14F are simultaneously turned on. Furthermore, outputs of the lasers 14A to 14F during the first sub-frame are different from outputs of the lasers 14A to 14F during the second sub-frame.

Types of observation modes and laser wavelength-specific image information required in the respective observation mode are the same as those in the first embodiment.

Color filters of three colors RGB are aligned at respective pixels of the color imager 26. Image information of a subject is accumulated as three pieces of data of RGB at the respective pixels. Three pieces of data are accumulated during each of the first sub-frame and the second sub-frame.

<Calculating Method>

The wavelengths of lights emitted from the six lasers during the first and second sub-frames are assumed to be L, M, N, O, P, and Q (nm), respectively.

Light quantities of the lights emitted from the six lasers during the first sub-frame are assumed to be $I_L$, $I_M$, $I_N$, $I_O$, $I_P$, and $I_Q$ (W), respectively.

Light quantities of the lights emitted from the six lasers during the second sub-frame are assumed to be $I_L'$, $I_M'$, $I_N'$, $I_O'$, $I_P'$, and $I_Q'$ (W), respectively.

Light receiving sensitivity characteristics of the respective color pixels to the applied lights having the six laser wavelengths in light receiving sensitivity characteristics are assumed to be $R_L$, $R_M$, $R_N$, $R_O$, $R_P$, $R_Q$, $G_L$, $G_M$, $G_N$, $G_O$, $G_P$, $G_Q$, $B_L$, $B_M$, $B_N$, $B_O$, $B_P$, $B_Q$ (A/W), respectively.

Reflection characteristics of a subject as a target with respect to the six laser wavelengths are determined to be $S_L$, $S_M$, $S_N$, $S_O$, $S_P$, and $S_Q$ (%), respectively.

Ratios of lights that effectively enter the imager in lights reflected from the subject as the target are assumed to be $V_L$, $V_M$, $V_N$, $V_O$, $V_P$, and $V_Q$, respectively.

As a result of imaging during the first sub-frame, signal values provided in accordance with the respective three color pixels of RGB are assumed to be $D_R$ (A), $D_G$ (A), and $D_B$ (A), and as a result of imaging during the second sub-frame, signal values provided in accordance with the respective three color pixels of RGB are assumed to be $D_R'$ (A), $D_G'$ (A), and $D_B'$ (A), respectively.

These parameters meet the following relationships.

$$D_R = I_L \times S_L \times V_L \times R_L + I_M \times S_M \times V_M \times R_M + I_N \times S_N \times V_N \times R_N + I_O \times S_O \times V_O \times R_O + I_P \times S_P \times V_P \times R_P + I_Q \times S_Q \times V_Q \times R_Q$$

$$D_G = I_L \times S_L \times V_L \times G_L + I_M \times S_M \times V_M \times G_M + I_N \times S_N \times V_N \times G_N + I_O \times S_O \times V_O \times G_O + I_P \times S_P \times V_P \times G_P + I_Q \times S_Q \times V_Q \times G_Q$$

$$D_B = I_L \times S_L \times V_L \times B_L + I_M \times S_M \times V_M \times B_M + I_N \times S_N \times V_N \times B_N + I_O \times S_O \times V_O \times B_O + I_P \times S_P \times V_P \times B_P + I_Q \times S_Q \times V_Q \times B_Q$$

$$D_R' = I_L' \times S_L \times V_L \times R_L + I_M' \times S_M \times V_M \times R_M + I_N' \times S_N \times V_N \times R_N + I_O' \times S_O \times V_O \times R_O + I_P' \times S_P \times V_P \times R_P + I_Q' \times S_Q \times V_Q \times R_Q$$

$$D_G' = I_L' \times S_L \times V_L \times G_L + I_M' \times S_M \times V_M \times G_M + I_N' \times S_N \times V_N \times G_N + I_O' \times S_O \times V_O \times G_O + I_P' \times S_P \times V_P \times G_P + I_Q' \times S_Q \times V_Q \times G_Q$$

$$D_B' = I_L' \times S_L \times V_L \times B_L + I_M' \times S_M \times V_M \times B_M + I_N' \times S_N \times V_N \times B_N + I_O' \times S_O \times V_O \times B_O + I_P' \times S_P \times V_P \times B_P + I_Q' \times S_Q \times V_Q \times B_Q$$

In these expressions, I, V, R, G, and B can be grasped in advance, and $D_R$, $D_G$, $D_B$, $D_R'$, $D_G'$, and $D_B'$ can be acquired in connection with the respective pixels by imaging. Thus, the above relational expressions are six simultaneous linear equations in which six types of unknowns, i.e., $S_L$, $S_M$, $S_N$, $S_O$, $S_P$ and $S_Q$ alone remain, and laser wavelength-specific reflectances for the respective pixels can be calculated. When the laser wavelength-specific reflectances are acquired in accordance with the respective pixels, they serve as two-dimensional laser wavelength-specific image information for the subject.

When noise is considerable, one frame may be divided into three or more, and the lasers 14A to 14F may be turned on in each of three or more sub-frames. In order to enhance the image reproducibility, it is considered that narrowing down to one solution by a redundant simultaneous linear equation is required.

Thus, assuming that color filters of an imaging device are provided for N colors, the number of pieces of laser wavelength-specific image information required for a selected observation mode is L, and the number of sub-frames in one frame is S, achieving N×S≥L is important.

[Effect]

Since the number of the lasers that are on during one sub frame is higher than the number of color separations of the color imager 26, a light quantity received by the color imager 26 increases. Thus, an exposure time during one sub-frame can be shortened, and moving image performance is improved. Furthermore, since the light quantity increases, noise is hardly produced when the light quantity provided by the color imager 26 is low, and the laser wavelength-specific image information can be accurately acquired. Thus, the reproducibility of images in various observation modes constructed from the structure is improved.

Third Embodiment

Figure 12:
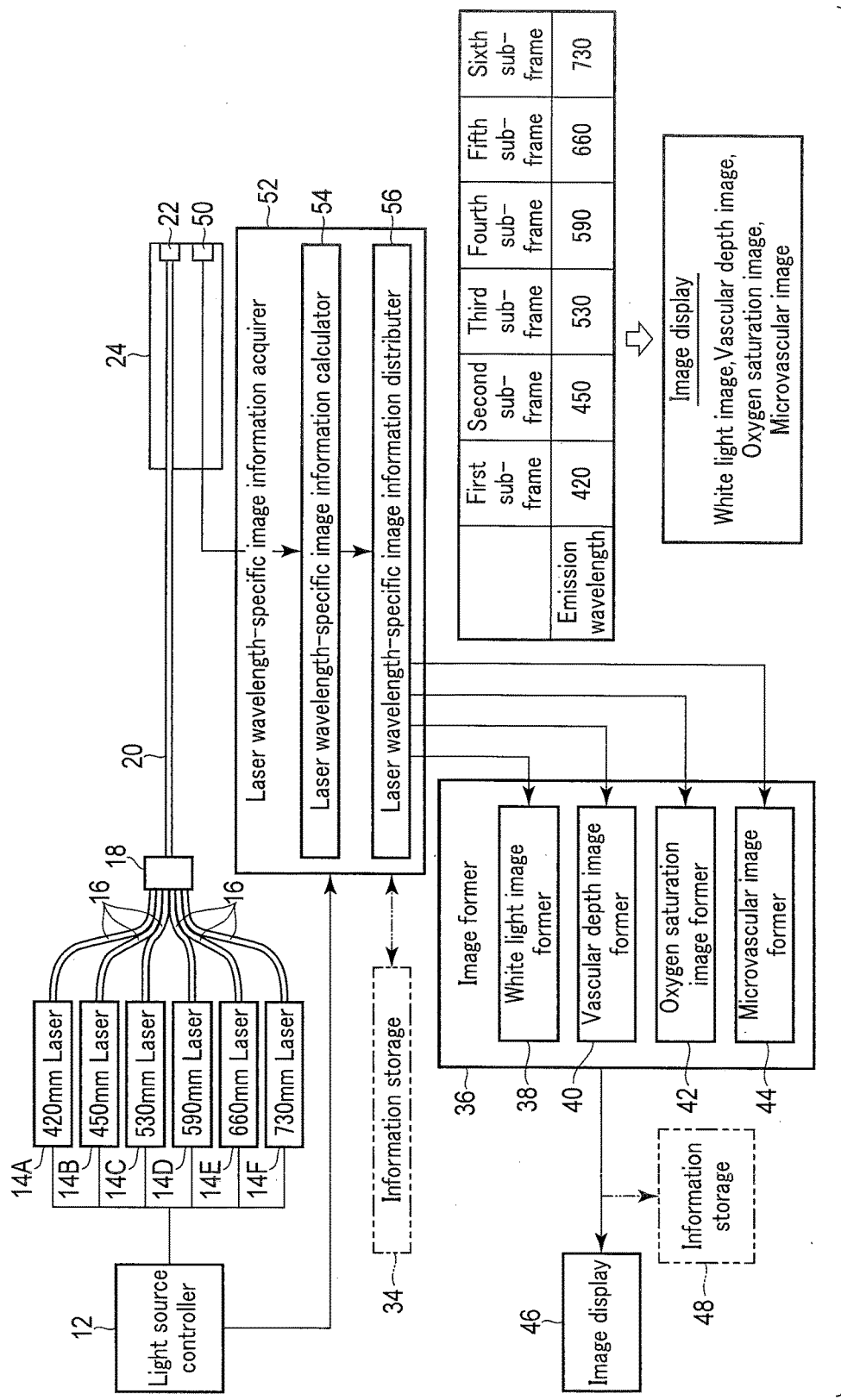
FIG. 12 shows an overall schematic view of an image forming apparatus according to a third embodiment.

This embodiment is an example in which a monochromatic imager that does not have a color separating function is used in place of the color imager using the color filters. FIG. 12 shows a schematic view of an overall apparatus.

In FIG. 12, members denoted by the same reference numerals as those for the members shown in FIG. 1 are like members, and a detailed description thereof will be omitted. Different parts will be mainly described hereinafter. That is, parts that are not described below are the same as those in the first embodiment.

[Configuration]

An image forming apparatus includes a monochromatic imager 50 to output an image signal upon receiving light from a subject, and a laser wavelength-specific image information acquirer 52 to acquire, from the image signal output from the monochromatic imager 50, pieces of laser wavelength-specific image information corresponding to central wavelengths of lights emitted from lasers 14A to 14F.

In the monochromatic imager 50, color filters are not provided on a front surface, one pixel forms one picture element, and light intensity information for returning light is received in accordance with each pixel (picture element).

The laser wavelength-specific image information acquirer 52 includes a laser wavelength-specific image information calculator 54 to calculate the pieces of laser wavelength-specific image information from the image signal output from the monochromatic imager 50, and a laser wavelength-specific image information distributer 56 to distribute and transmit the calculated laser wavelength-specific image information to image formers 38, 40, 42, and 44.

[Operation]
<Drive Method>

In this embodiment, one frame is constituted of sub-frames of six periods, i.e., a first sub-frame, a second sub-frame, a third sub-frame, a fourth sub-frame, a fifth sub-frame, and a sixth sub-frame.

During the first sub-frame, the laser 14A to emit light having a wavelength of 420 nm is turned on. During the second sub-frame, the laser 14B to emit light having a wavelength of 450 nm is turned on. During the third sub-frame, the laser 14C to emit light having a wavelength of 530 nm is turned on. During the fourth sub-frame, the laser 14D to emit light having a wavelength of 590 nm is turned on. During the fifth sub-frame, the laser 14E to emit light having a wavelength of 660 nm is turned on. During the sixth sub-frame, the laser 14F to emit light having a wavelength of 730 nm is turned on.

<Observation Modes>

In this embodiment, like the first embodiment, it is possible to select a total of four types, i.e., a normal observation mode, a vascular depth observation mode, an oxygen saturation observation mode, and a microvascular observation mode.

In the normal observation mode, a white light image is constructed from a 450-nm image acquired during the second sub-frame, a 530-nm image acquired during the third sub-frame, and a 660-nm image acquired during the fifth sub-frame.

In the vascular depth observation mode, a vascular depth image is constructed from the 450-nm image acquired during the second sub-frame and the 660-nm image acquired during the fifth sub-frame.

In the oxygen saturation observation mode, an oxygen saturation image is constructed from the 530-nm image acquired during the third sub-frame and a 730-nm image acquired during the sixth sub-frame.

In the microvascular observation mode, a microvascular image is constructed from a 420-nm image acquired during the first sub-frame.

The number of all the pieces of the laser wavelength-specific image information required for a selected observation image is six, one frame is thus constituted of the sub-frames of six periods during which the lights having the six wavelengths are applied, and hence six independent simultaneous linear equations can be created to the respective wavelengths from data of each of the pixels, thereby acquiring the respective pieces of laser wavelength-specific image information.

<Calculation Method>

A calculation method of the laser wavelength-specific image information performed by the laser wavelength-specific image information calculator 54 will now be described.

A wavelength of light emitted from a laser that is turned on during one sub-frame is assumed to be L(nm).

A light quantity of lights emitted from the lasers during one sub-frame is assumed to be $I_L$ (W).

Light receiving sensitivity characteristics of the imager to an applied laser wavelength are assumed to be $M_L$ (A/W).

Reflection characteristics of a subject as a target to light having a laser wavelength is assumed to be $S_L$ (%).

In the light reflected from the subject as the target, a ratio of light that effectively enters the monochromatic imager 50 is assumed to be $V_L$ (%).

A signal value obtained in accordance with each pixel as a result of imaging is assumed to be D (A).

These parameters meet the following relationship.

$$D = I_L \times S_L \times V_L \times M_L$$

Like the first embodiment, $I_L$, $V_L$, and $M_L$ can be grasped in advance, and D can be acquired in connection with each pixel by imaging. Thus, an independent linear equation in which only one unknown $S_L$ remains is provided, and the laser wavelength-specific reflectances for the respective pixels can be calculated.

The calculated laser wavelength-specific image information is distributed and transmitted to the image formers 38, 40, 42, and 44 in the image former 36 by the laser wavelength-specific image information distributer 56. The distribution and transmission by the laser wavelength-specific image information distributer 56 is carried out like the laser wavelength-specific image information distributer 56 in the first embodiment.

A subsequent process of image formation in the image formers 38, 40, 42, and 44 and a process of image display performed by an image display 46 are the same as those in the first embodiment.

[Others]

In order to acquire image information having higher image reproducibility, the same laser may perform irradiation more than once during one frame. More accurate image information can be provided by solving the six unknowns with the use of seven or more independent linear equations rather than solving the six respective independent linear equations to the six unknowns as described above. Particularly, when an apparatus is used for a use application where a subject is restricted, there may be a wavelength that is prone to generation of an error in image information. In such a case, more accurate laser wavelength-specific image information can be calculated by applying light having the laser wavelength while changing a light quantity more than once or without changing the same.

[Effect]

Since the monochromatic imager 50 is used, the pixels function as picture elements as they are, and resolution enhancement can be performed higher than the color imager 26.

Of the constants that can be grasped in advance, there is no constant concerning color filters, a data error deriving from an error concerning the numerical value is not produced, and hence image reproducibility is high.

Although the number of the sub-frames is increased, since high-speed modulation with a high light quantity is possible as the only characteristic of the lasers, a time of one frame can be shortened, and moving image performance is not deteriorated too much.

Although the embodiments according to the present invention have been described with reference to the drawings, the present invention is not restricted to these embodiments, and various modifications or changes may be made without departing from a gist of the invention. The various modifications or changes described herein include embodiments provided by appropriately combining the foregoing embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image forming apparatus comprising:
a plurality of lasers, wherein each of the plurality of lasers is configured to emit light having a different central wavelength to irradiate a subject;
an image sensor; and
a processor comprising hardware, wherein the processor is configured to:
  receive a selection of a plurality of observation modes, wherein each of the plurality of observation modes corresponds to a different type of optical information of the subject;
  in each of a plurality of sub-frame periods of one frame period,
    control a different group of lasers to emit the lights of the different central wavelengths corresponding to the lasers of the different group of lasers to irradiate the subject; and
    control the image sensor to photoelectrically convert light received from the subject to generate an image signal;
  acquire, from the image signal generated by the image sensor in the each of the plurality of sub-frame periods, pieces of wavelength-specific image information corresponding to the different central wavelengths of the lights emitted by the different group of lasers;
  generate a first observation image signal including first observation image information corresponding to a first observation mode of the plurality of observation modes selected, based on a piece of wavelength-specific image information acquired from the image signal generated by the image sensor in a first sub-frame period of the plurality of sub-frame periods; and
  generate a second observation image signal including second observation image information corresponding to a second observation mode of the plurality of observation modes selected, based on the piece of wavelength-specific image information acquired from the image signal generated by the image sensor in the first sub-frame period of the plurality of sub-frame periods,
wherein the image sensor and the processor are configured to satisfy a relationship: $N \times S \geq L$,
  where N is a number of types of pixels of the image sensor with different wavelength sensitivity,
  where L is a number of the pieces of the wavelength-specific image information, and
  where S is a number of the plurality of sub-frame periods of the one frame period.

2. The image forming apparatus according to claim 1, wherein a number of the different central wavelengths of the lights emitted by the different group of lasers in the each of the plurality of sub-frame periods on the one frame period is smaller than N.

3. An image forming apparatus comprising:
a plurality of lasers, wherein each of the plurality of lasers is configured to emit light having a different central wavelength to irradiate a subject;
an image sensor; and
a processor comprising hardware, wherein the processor is configured to:
  receive a selection of a plurality of observation modes, wherein each of the plurality of observation modes corresponds to a different type of optical information of the subject;

in each of a plurality of sub-frame periods of one frame period, control a different group of lasers to emit the lights of the different central wavelengths corresponding to the lasers of the different group of lasers to irradiate the subject; and control the image sensor to photoelectrically convert light received from the subject to generate an image signal, wherein one of the different group of lasers comprises lasers of the plurality lasers configured to emit lights that are mixed to serve as illumination light suitable for a normal observation mode as a first observation mode;

acquire, from the image signal generated by the image sensor in the each of the plurality of sub-frame periods, pieces of wavelength-specific image information corresponding to the different central wavelengths of the lights emitted by the different group of lasers;

generate a first observation image signal including first observation image information corresponding to the first observation mode of the plurality of observation modes selected, based on a piece of wavelength-specific image information acquired from the image signal generated by the image sensor in a first sub-frame period of the plurality of sub-frame periods; and generate a second observation image signal including second observation image information corresponding to a second observation mode of the plurality of observation modes selected, based on the piece of wavelength-specific image information acquired from the image signal generated by the image sensor in the first sub-frame period of the plurality of sub-frame periods, wherein the image sensor and the processor are configured to satisfy a relationship: $N \times S \geq L$, where N is a number of types of pixels of the image sensor with different wavelength sensitivity, where L is a number of the pieces of the wavelength-specific image information, and where S is a number of the plurality of sub-frame periods of the one frame period.

4. The image forming apparatus according to claim 3, wherein the processor is configured to control a display to display the first observation image information corresponding to the first observation mode and the second observation image information corresponding to the second observation mode simultaneously based on the first observation image signal and the second observation image signal.

5. The image forming apparatus according to claim 3, wherein the processor is configured to:

retrieve, from a storage, information to select pieces of wavelength-specific image information for generating the first observation image signal corresponding to the first observation mode, from the pieces of wavelength-specific image information acquired; and in response to the selection of the second observation mode, retrieve, from the storage, information to select pieces of wavelength-specific image information for generating the second observation image signal corresponding to the second observation mode, from the pieces of wavelength-specific image information acquired.

6. An image forming apparatus comprising:

a plurality of lasers, wherein each of the plurality of lasers is configured to emit light having a different central wavelength to irradiate a subject;

an image sensor; and a processor comprising hardware, wherein the processor is configured to:

receive a selection of a plurality of observation modes, wherein each of the plurality of observation modes corresponds to a different type of optical information of the subject;

in each of a plurality of sub-frame periods of one frame period, control a different group of lasers comprising at least two lasers of the plurality of lasers to simultaneously emit the lights of the different central wavelengths corresponding to the at least two lasers to irradiate the subject; and control the image sensor to photoelectrically convert light received from the subject to generate an image signal;

acquire, from the image signal generated by the image sensor in the each of the plurality of sub-frame periods, pieces of wavelength-specific image information corresponding to the different central wavelengths of the lights emitted by the different group of lasers; and generate a first observation image signal including first observation image information corresponding to a first observation mode of the plurality of observation modes selected, based on a piece of wavelength-specific image information acquired from the image signal generated by the image sensor in a first sub-frame period of the plurality of sub-frame periods; and generate a second observation image signal including second observation image information, corresponding to a second observation mode of the plurality of observation modes selected, based on the piece of wavelength-specific image information acquired from the image signal generated by the image sensor in the first sub-frame period of the plurality of sub-frame periods, wherein the image sensor and the processor are configured to satisfy a relationship: $N \times S \geq L$, where N is a number of types of pixels of the image sensor with different wavelength sensitivity, where L is a number of the pieces of the wavelength-specific image information, and where S is a number of the plurality of sub-frame periods of the one frame period.

7. The image forming apparatus according to claim 6, wherein the number of the plurality of sub-frames of the one frame period is different from a number of the plurality of observation modes selected.

8. The image forming apparatus according to claim 7, wherein the number of the plurality of sub-frames of the one frame period is less than the number of the plurality of observation modes selected.

* * * * *